United States Patent
Hirakui

(10) Patent No.: US 8,152,142 B2
(45) Date of Patent: Apr. 10, 2012

(54) SERVICE WATER PIPE FAUCET DIRECT-CONNECTED OZONE WATER PRODUCER WITH SELF-POWER GENERATOR

(75) Inventor: Kenzo Hirakui, Yaita (JP)

(73) Assignee: Nissho Engineering Co., Ltd., Yaita (JP)

( * ) Notice: Subject to any disclaimer, the term of this patent is extended or adjusted under 35 U.S.C. 154(b) by 516 days.

(21) Appl. No.: 12/310,824

(22) PCT Filed: Oct. 5, 2006

(86) PCT No.: PCT/JP2006/319934
§ 371 (c)(1),
(2), (4) Date: Mar. 9, 2009

(87) PCT Pub. No.: WO2008/044262
PCT Pub. Date: Apr. 17, 2008

(65) Prior Publication Data
US 2010/0001418 A1    Jan. 7, 2010

(51) Int. Cl.
*B01F 3/04* (2006.01)
(52) U.S. Cl. .................. 261/25; 261/84; 261/DIG. 42
(58) Field of Classification Search .................. 261/25, 261/27, 79.2, 84, DIG. 42, DIG. 75
See application file for complete search history.

(56) References Cited

U.S. PATENT DOCUMENTS

| | | | | | |
|---|---|---|---|---|---|
| 2,778,800 | A | * | 1/1957 | Sheahan | 261/49 |
| 4,049,552 | A | * | 9/1977 | Arff | 210/192 |
| 4,230,571 | A | * | 10/1980 | Dadd | 210/760 |
| 4,656,010 | A | * | 4/1987 | Leitzke et al. | 422/186.18 |
| 4,900,481 | A | * | 2/1990 | Kishioka | 261/64.4 |
| 5,871,701 | A | * | 2/1999 | Long | 422/186.18 |
| 6,030,586 | A | * | 2/2000 | Kuan | 422/186.07 |
| 6,521,194 | B2 | * | 2/2003 | Yeh | 422/186.12 |
| 6,534,023 | B1 | * | 3/2003 | Liou | 422/186.18 |
| 6,808,637 | B2 | * | 10/2004 | Cho | 210/744 |
| 7,022,225 | B1 | * | 4/2006 | Clawson et al. | 210/188 |
| 2005/0189770 | A1 | * | 9/2005 | Baarman et al. | 290/43 |
| 2006/0266683 | A1 | * | 11/2006 | Sung | 210/198.1 |

FOREIGN PATENT DOCUMENTS

| | | |
|---|---|---|
| JP | 63-25204 A | 2/1988 |
| JP | HEI-3-43398 | 4/1991 |
| JP | 2000-348848 A | 12/2000 |
| JP | 2003-155970 A | 3/2003 |
| JP | 2003135944 A | 5/2003 |
| JP | 2003-209212 | 7/2003 |
| JP | 2003320232 A | 11/2003 |
| JP | 2005-169297 A | 12/2003 |

* cited by examiner

*Primary Examiner* — Charles Bushey

(57) ABSTRACT

An apparatus for producing water having dissolved ozone therein of the type direct-connectable to a pressurized-water supply faucet (26) includes a nozzle (5) for directing a flow of pressurized water from the supply faucet (26) to a turbine (1) to effect rotation thereof, the turbine (1) having magnets (13) attached thereto magnetically coupled to corresponding magnets (13) attached to a disc (14) of a power generator (3). Rotation of the turbine (1) is magnetically coupled to the power generator (3) to generate electrical power for supply to an ozone generator to generate ozone for combination with the so-supplied water to produce ozonated water.

6 Claims, 7 Drawing Sheets

SERVICE WATER PIPE FAUCET DIRECT-CONNECTED OZONE WATER PRODUCER WITH SELF-POWER GENERATOR

TECHNICAL FIELD

This invention relates to an equipment for applying ozone to service water to produce ozone water.

BACKGROUND ART

In order to produce ozone water, it has been employed as its simple method, to produce ozone through voiceless electric discharging system or plane electric discharging system, agitated and admixed ozone and water and generate ozone water. As a practical process, commercial external electric power is employed as electric power for an ozone generator and this electric power is applied as discharging electric power for generating ozone.

Accordingly, in the case that the equipment described above is to be installed, an electrical work concerning wiring cannot be avoided, and it is frequently found that an available electric power supply outlet is not present near the installed equipment and in particular, in the case of an outdoor installation, electric power supply wiring work cannot be avoided. In addition, since water and commercial electric power are used while they are adjacent to each other, taking safety phase into consideration cannot be avoided.

Further, although this equipment is useful in this method merely in view of its convenience to use external electric power, the equipment merely utilizing external electric power is contrary to presence of superior equipment in one hand and becoming to produce harmful substance in the other hand in a trend of study for a nowadays environmental issue, natural energy issue in particular, resulting in that this equipment is hardly to be judged as the total superior equipment.

In view of the foregoing, in order to overcome the most important problem found in this equipment, this invention aims at development of the equipment enabling problem to be resolved by taking no electric power consumed by the ozone generator from the external power source, but by utilizing electric power got from the power generator stored in the equipment described above.

Patent Document 1: Japanese Patent Unexamined Publication No. 2003-320232
Patent Document 2: Japanese Patent Unexamined Publication No. 2003-135944

DISCLOSURE OF INVENTION

Problem to be Solved by Invention

Problems to be solved by the present invention consist in no supplying of electric power from the external power source, so that they consist in performing high efficient and stable electric power generating operation within the equipment described above and usage of electric power as electric power for producing ozone.

Means for Solving Problems

A high efficient electric power generating method that cannot be avoided in the course of developing the present invention can be realized by applying an electric power generating method disclosed in Japanese Patent Application No. 2003-209212 that has already been filed. Further, In order to attain a high output electric power, it becomes necessary to have a function enabling a high torque and high speed rotation of a water flow turbine to be attained.

Effects of Invention

A number of accidents with contamination of colon *bacillus, staphylococcus aureus* and *salmonella* represented by O-157 have been reported in recent years and as a method capable of easily overcoming these bacteria, cleaning by ozone water is made effective. Along with this trend, although a number of apparatuses for use in changing service water into ozone water have been developed, all of these apparatuses are operated through supplying electric power from an external power source, and when no power source is present near the apparatus installation site, an electrical wiring work cannot be avoided.

Since the service water pipe faucet direct-connected ozone water producer with a water-flow power generator is operated by a method for producing ozone with electric power attained through electric power generation under utilization of self-produced discharged water flow pressure, this producer is an ozone water producer capable of eliminating the aforementioned defaults and being installed at a faucet placed at any locations where a water pressure of a certain pressure or more is present.

Figure 1:
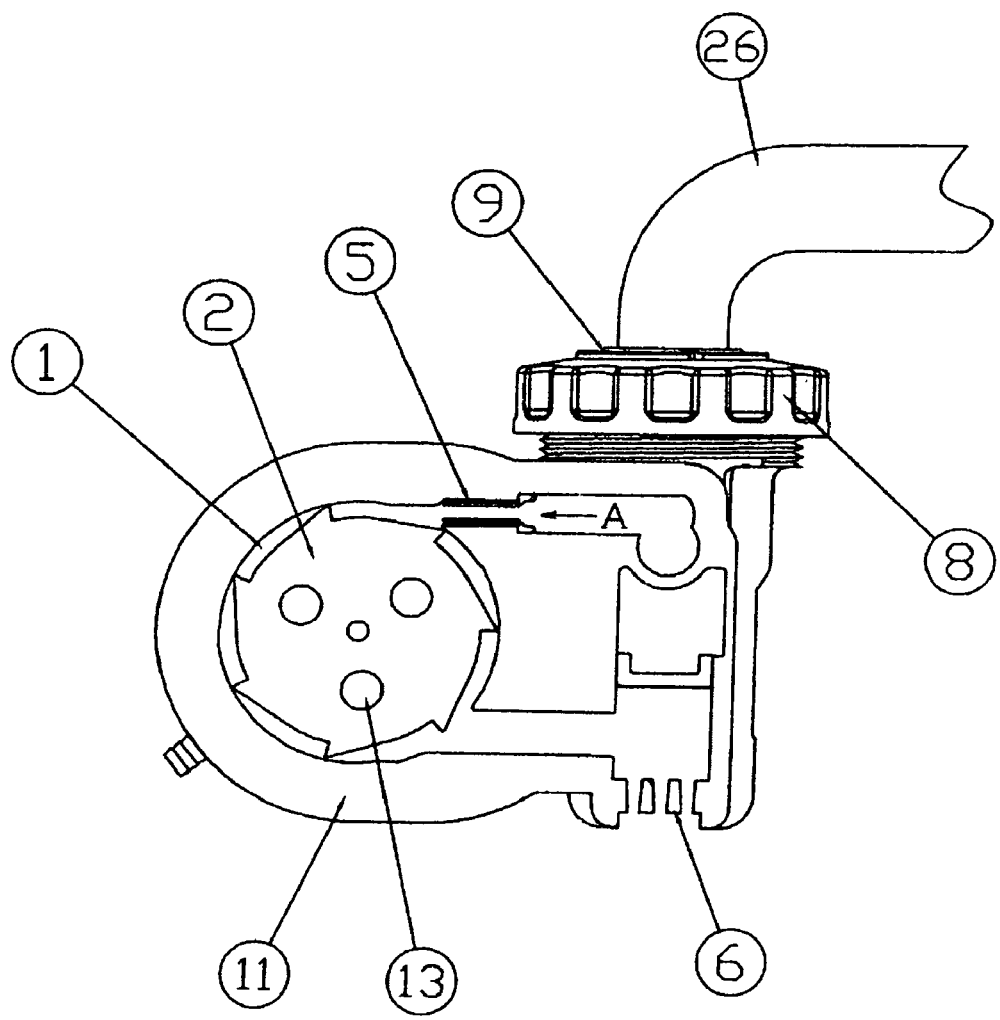
FIG. 1 is a sectional view for showing a water path in the present invention (Embodiment 1).

| DESCRIPTION OF REFERENCE NUMERALS | |
|---|---|
| 1 | turbine chamber |
| 2 | turbine |
| 3 | power generator |
| 4 | ozone generator |
| 5 | nozzle |
| 5a | sectional view of nozzle |
| 5b | outside hole of nozzle |
| 6 | port |
| 7 | lever |
| 8 | attaching-fixing screw |
| 9 | fixing ring |
| 10 | raw water port |
| 11 | storing case with turbine chamber |
| 12 | drying agent case |
| 13 | magnet |
| 14 | disk |
| 15 | turbine chamber closing lid |
| 16 | power generator attaching seat |
| 17 | container lid |
| 18 | glass pipe |
| 19 | fitting for turning-on electricity |
| 20 | hollow holder |
| 21 | coil-like electrode |

-continued

| | DESCRIPTION OF REFERENCE NUMERALS |
|---|---|
| 22 | supporting part |
| 23 | large diameter glass pipe |
| 24 | fine diameter glass pipe |
| 25 | fitting for turning-on electricity |
| 26 | service water pipe faucet |

BEST MODE FOR CARRYING OUT INVENTION

Since the present invention relates to a method for fixing an ozone water producer to a service water pipe faucet, it is necessary that its size is set to a compact size as small as possible. The electric power is generated by connecting the ozone water producer to water supplying port of a service water pipe faucet with a thread fitting method, guiding a discharging water flow to a turbine chamber (1) inside the equipment, rotating a turbine (2) installed in the turbine chamber (1) and rotating the power generator (3) for making synchronization with the turbine. Accordingly, as a method for storing the power generator (3) and an ozone generator (4) within a case, and for feeding ozone gas into water, it is possible to realize water discharging from a port (6) as ozone water while water is being mixed at the turbine chamber at the same time as discharging water under utilization of a negative pressure when water is discharged through a nozzle (5) for use in making a high-speed rotation of the turbine.

Embodiment 1

When the present invention is to be carried out, a small-sized three-phase AC power generation can be performed by basically employing a power generating method disclosed in Japanese Patent Application No. 2003-209212 that has already been filed, so that a high efficient electric power generation can be easily realized.

FIG. 1 is a sectional view for showing a water flow path, wherein water flowed in through a service water pipe faucet (26) flows along an arrow A indicated in this figure and flows out toward the port (6) while rotating the turbine (2). The most important thing in this case consists in outputting both a torque for rotating the turbine and its high-speed rotation. As the first invention of the equipment, the nozzle (5) shown in FIG. 2 capable of narrowing a water flow path just before the turbine, increasing a water pressure, injecting water and rotating the turbine at a high speed is assembled into this equipment, thereby the power generator can be rotated at a high speed and a high torque, and a stable electric power generation can be realized.

Figure 2:
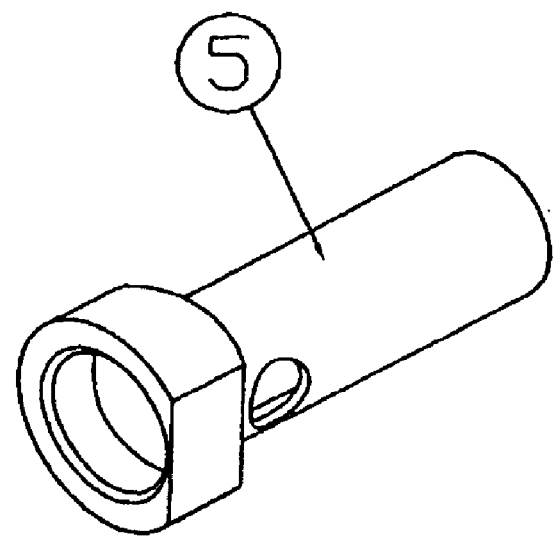
FIG. 2 is an outer appearance view and a sectional view of a nozzle in the present invention (Embodiment 1).
Figure 2:
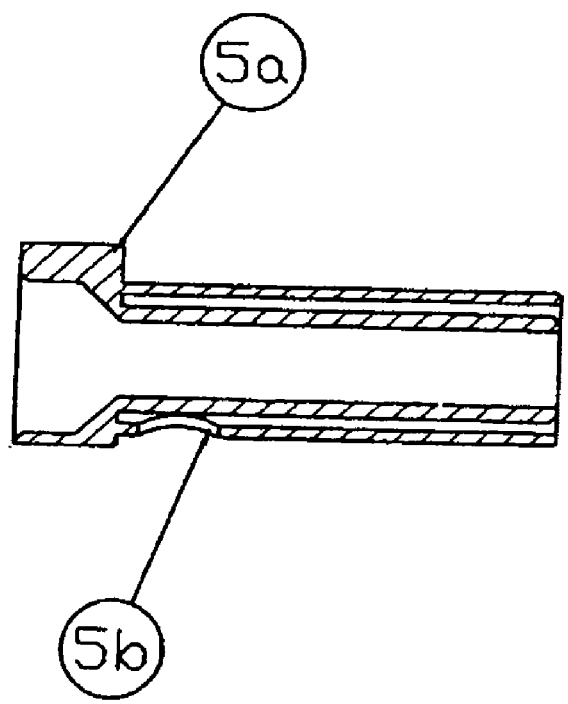

Further, the nozzle (5) is of a hollow double pipe like as shown in the sectional view (5a) in FIG. 2, wherein when a lateral hole is formed at an outer pipe and water is flowed at the inner diameter part of an inner pipe to discharge water, a negative pressure is generated at the hollow part, so that ozone gas is easily sucked through the hole (5b) formed at the outer pipe and then ozone mixed water can be discharged from the port while ozone is being mixed with the water discharged through the nozzle and the turbine is being rotated by it.

Figure 3:
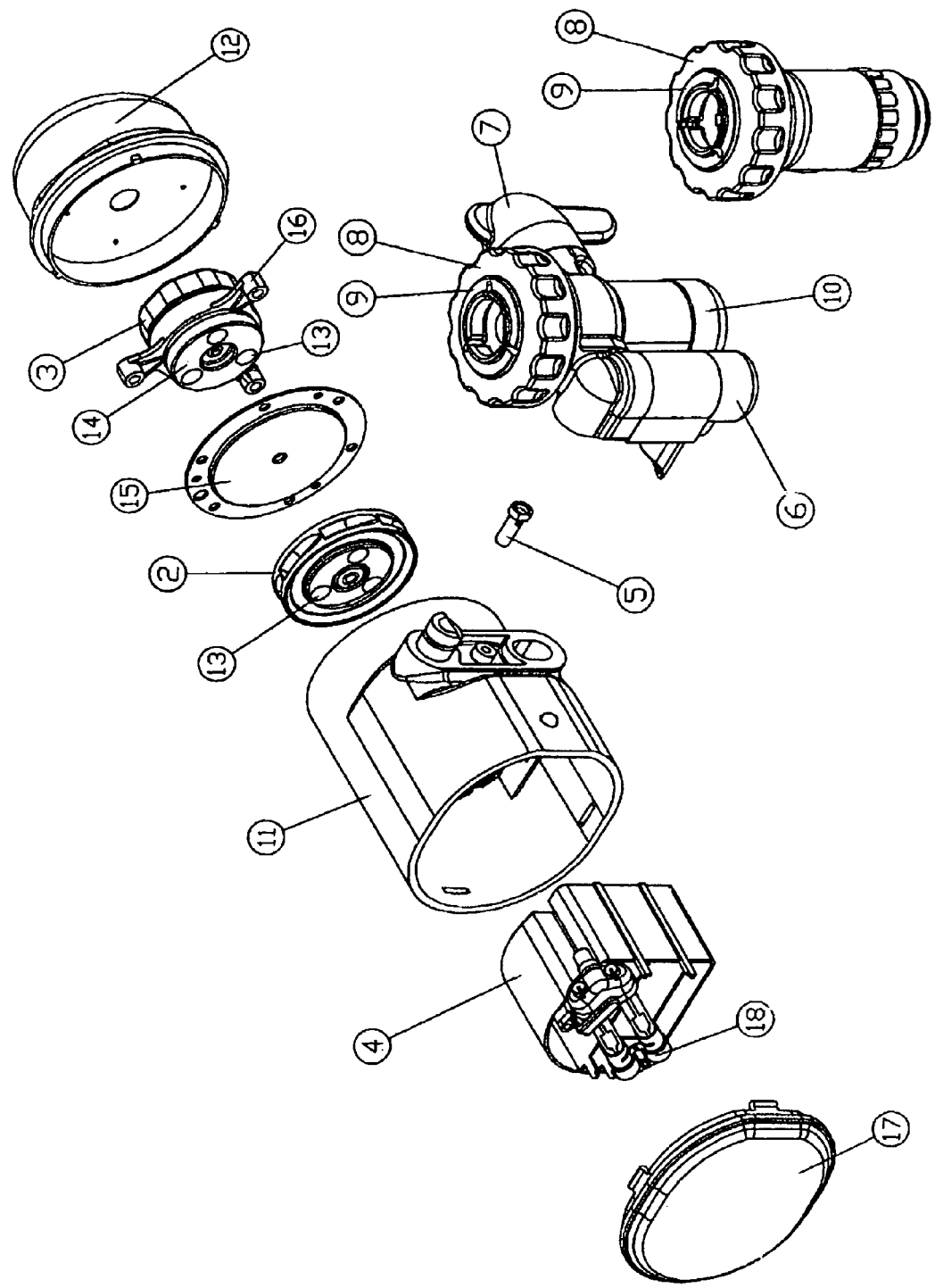
FIG. 3 is a development view for showing a configuration of component parts in the present invention (Embodiment 1).
Figure 4:
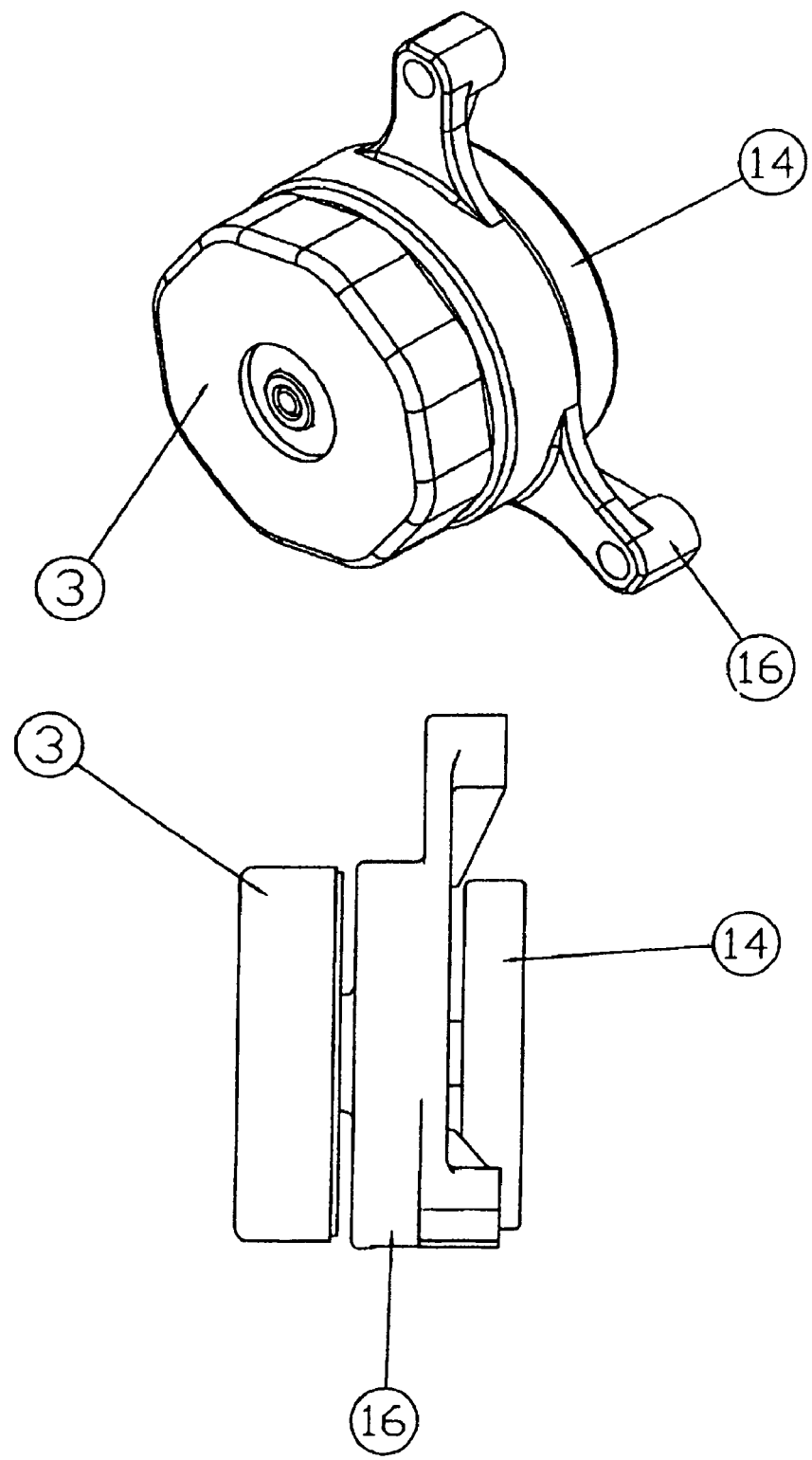
FIG. 4 is a view for showing a power generator part in the present invention (Embodiment 1).

As the second invention, FIG. 3 is a developed view for showing a configuration of component parts of the present invention, this is roughly comprised of a power generator (3) in FIG. 4, a storing case with a turbine chamber (11), the ozone generator (4), the turbine (2) and a drying agent case (12) storing drying agent, wherein the power generator (3) is provided with a disk (14) making synchronization with magnets (13) arranged at the turbine (2), the disk is also provided with the magnets (13) arranged in the same manner as that for the turbine, and the power generator is rotated synchronously with rotation of the turbine. An important thing to be noted consists in insertion of the turbine (2) into the storing case with the turbine chamber (11), applying a seal for preventing a water leakage and a sealed closing of it with a turbine chamber closing lid (15) and a clearance between the turbine (2) and the disk (14) of the power generator is made narrow as much as possible to enable a synchronization between the turbine (2) and the disk (14) of the power generator to be realized without any trouble.

Figure 5:
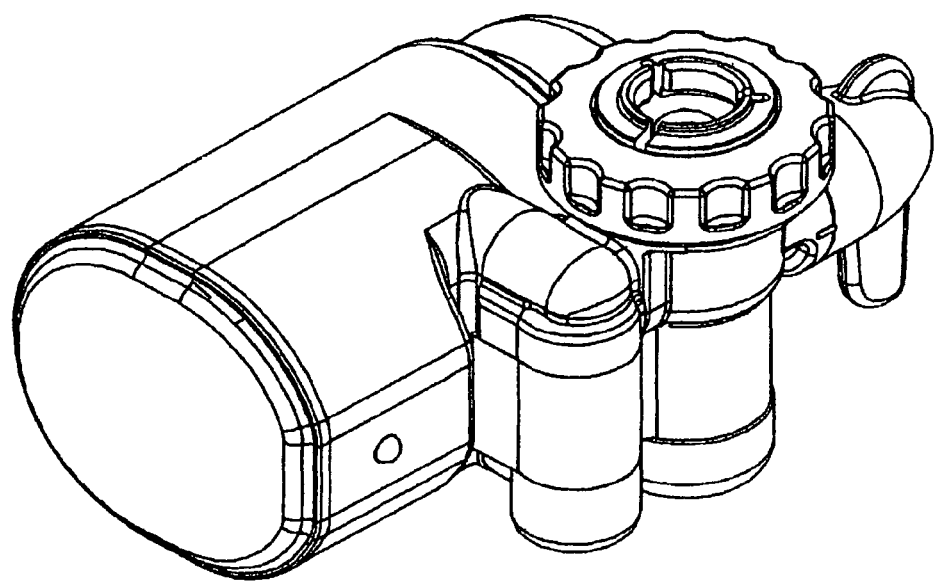
FIG. 5 is an outer appearance view for showing the present invention (Embodiment 1).
Figure 6:
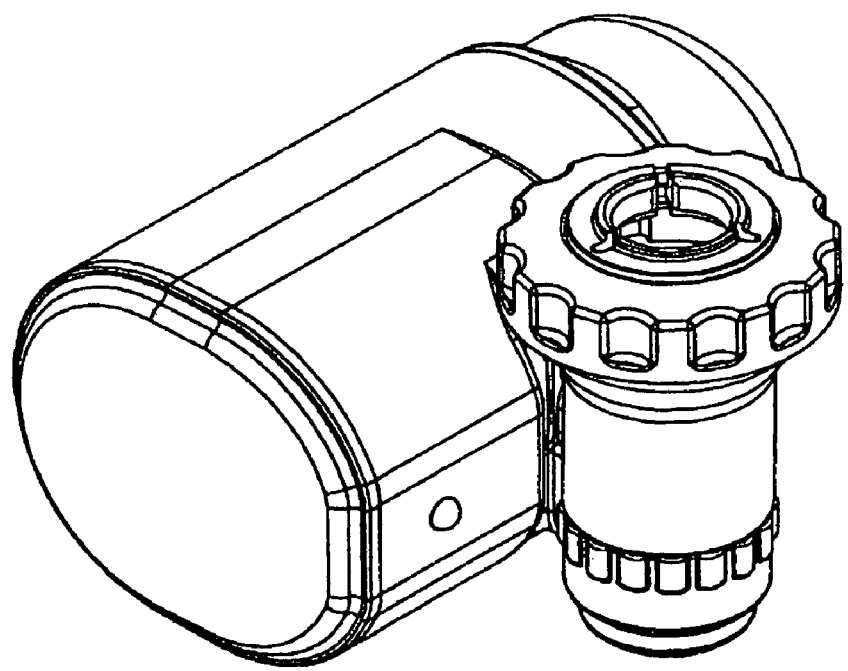
FIG. 6 is an outer appearance view for showing the present invention (Embodiment 1).

As the third invention, FIGS. 5 and 6 are outer appearance views for showing the present invention with a system of full-time power generator driving in the time of discharging water, a method for forcedly flowing water to the turbine chamber (1) and rotating the turbine (2) to enable the power generator to be driven and a method for making an easy modification of the system through mere replacement of partial component parts, and FIG. 6 shows a system of a type in which water is always fed to the turbine chamber when water is discharged, so that the power generator becomes an operated state and only occurrence of ozone gas is changed over through an electrical turned-on or turned-off state of a switch.

FIG. 5 is a view for showing a system of one type in which a water flow is guided to the turbine chamber (1) to drive the turbine (2), the power generator (3) is rotated synchronously to generate electric power, and the other type in which a lever (7) of this equipment is turned directly to cause a spool to be moved and service water is discharged to a raw water port (10) of this equipment.

Employment of this method causes a multiplicity of this equipment to be generated, FIG. 5 shows an assumption in which although ozone water is needed, a service water is desired to be mainly used and FIG. 6 shows an assumption in which it is mainly desired to use ozone water, wherein since a mere replacement of partial component parts is sufficient for each of the operations, its production cost may also be reduced and both of these systems enable the product of the present invention to be fixed to a service water pipe faucet by fastening a ring (9) for fixing the service water pipe faucet installed inside the equipment through an attaching-fixing screw (8).

Figure 7:
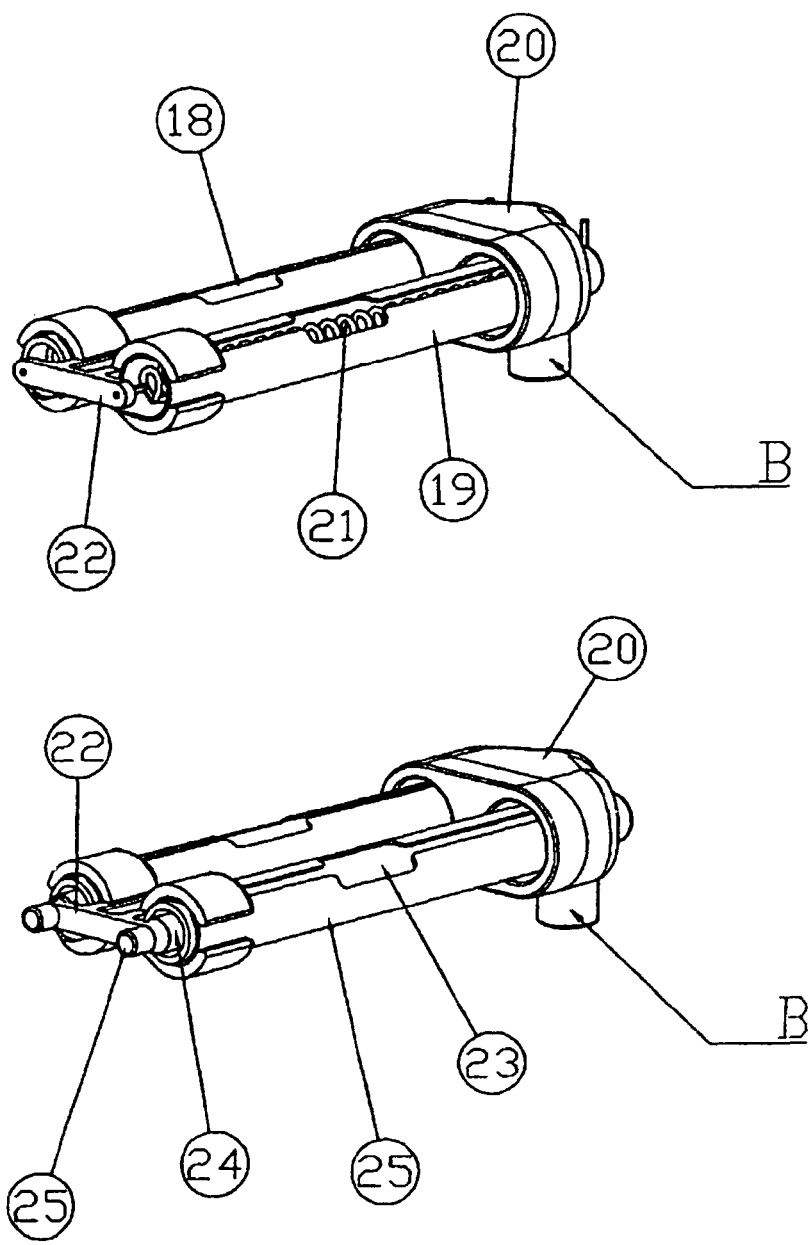
FIG. 7 is a view for showing an ozone generator part in the present invention (Embodiment 1).

As the fourth invention, there is provided an ozone generator part shown in FIG. 7. This equipment is constituted by the drying agent case (12), the storing case with the turbine chamber (11) containing the turbine (2), the power generator (3), the ozone generator (4) therein, and the case lid (17) for sealing this equipment. However, since it is necessary to flow the generated ozone gas, it is not possible to make a complete sealingly-closed state. In the case of this equipment, a hole for use in taking surrounding air into this equipment is arranged at the drying agent case (12), the surrounding air flows through the hole, the flowed-in surrounding air reaches to a position of the ozone generator part through a space having the drying agent stored therein, so that dried surrounding air is taken into the equipment. However, employment of a glass pipe (18) showing a slight high-resistant force against high humidity enables efficient ozone gas to be generated.

However, although this is a structure in which the glass pipe (18) is supported by the hollow holder (20), a fitting for turning-on electricity (19) is arranged outside the glass pipe, a coil-like electrode (21) made of stainless steel is arranged inside the glass pipe, an electric discharge is carried out inside the glass pipe to generate ozone, part B in the hollow holder (20) and the nozzle (5) are connected by a tube, ozone produced by a negative pressure generated at the nozzle (5) flows into the nozzle, it becomes an effective means to provide a high insulative supporting element (22) having an inner diameter of the glass pipe and inner diameters of the stainless steel coil and the glass pipe concentrically arranged.

Further, as the ozone generator part for avoiding a deterioration of electric discharging of the stainless steel coil-like electrode (21), it is possible to provide an ozone generator part in which that a fine diameter glass pipe (24) is concentrically inserted into the large diameter glass pipe (23), and that fittings for turning-on electricity (25) are arranged each of outside the large diameter glass pipe and inside the fine diameter glass pipe, respectively, and the glass pipes discharge to each other to enable it to be durable against longer hours discharging. Provided that which one of the ozone generator part is used should be determined in response to a price of the product.

The product of the present invention has concurrently a function acting as an ozone water producer as well as a function in which it can be simply applied to another application as an easy hydroelectric power generator.

INDUSTRIAL APPLICABILITY

In view of the aforementioned configuration, the present invention provides the ozone water producer not requiring any feeding of external electric power at all in which an electric power is produced by rotating the power generator under utilization of a pressure of discharged water through releasing of the service water pipe faucet, ozone is produced with the electric power, and this ozone is agitated and admixed with water rotated the power generator to enable ozone water to be produced.

What is claimed is:

1. An apparatus for direct connection to a pressurized-water supply faucet for producing a supply of ozonated water to an ozonated-water discharge port, comprising:
    a rotatably mounted turbine wheel within a fluid-tight turbine chamber having a wall surface on one lateral side of the turbine wheel,
    a plurality of magnets attached to a portion of the turbine wheel;
    a nozzle for directing a stream of pressurized supply water to the turbine wheel to effect rotation thereof;
    an electrical power generator for generating electrical power in response to rotation of a rotatable part thereof, the rotatable part having a plurality of magnets attached thereto, the magnets of the turbine wheel and the magnets of the rotatable part magnetically coupled through the wall so that rotation of the turbine wheel in response to the stream of pressurized supply water from the nozzle causes rotation of the rotatable part of the electrical power generator to generate electrical power; and
    an ozone generator connected to the electrical power generator to receive electrical power therefrom and generate ozone for supply to the nozzle;
    the nozzle having a hole or opening for therein for admitting ozone from the ozone generator into the supply water to form ozonated water for discharge through the ozonated water discharge port.

2. The apparatus of claim 1, wherein the nozzle further comprises,
    a double-wall nozzle having inner and outer spaced-apart walls defining a space therebetween, the outer wall having an opening therethrough for admitting ozone into the space therebetween for mixing into the pressurized supply water to form a stream of ozonated water directed to the turbine wheel to effect rotation thereof.

3. An apparatus for direct connection to a pressurized-water supply faucet for producing a supply of ozonated water to a discharge port, comprising:
    an electrical power generator driven by a rotatable turbine wheel for generating electrical power in response to rotation of the turbine wheel, the turbine wheel mounted for rotation within a fluid-tight turbine chamber having a wall surface on one lateral side of the turbine wheel, the turbine wheel having at least two magnets attached thereto facing the wall surface, the electrical power generator having a rotatable part adjacent the wall surface having at least two magnets attached thereto facing the wall surface on the side opposite the turbine wheel, the magnets of the turbine wheel and the magnets of the rotatable part magnetically coupled so that rotation of the turbine wheel causes rotation of the rotatable part of the electrical power generator to generate electrical power;
    an ozone generator connected to the electrical power generator to receive electrical power therefrom and generate ozone; and
    a nozzle for directing a stream of pressurized supply water to the turbine wheel to effect rotation thereof and connected to the ozone generator to introduce ozone into the stream of pressurized supply water.

4. A system for direct connection to a pressurized-water supply faucet for providing a supply of non-ozonated water or a supply of ozonated water and adaptable to at least two configurations, comprising:
    a primary housing having
        a rotatable turbine wheel in a fluid-tight turbine chamber, the chamber having a wall on one lateral side of the turbine wheel,
        an electrical generator for supplying electricity and having a rotatable part on the other lateral side of the wall, the rotatable turbine wheel having magnets attached thereto and the rotatable part of the electrical generator having corresponding magnets attached thereto, the magnets magnetically coupled through the wall of the fluid-tight turbine chamber,
        an ozone generator for generating ozone in response to electricity supplied from the electrical generator,
        a nozzle for directing a flow of pressurized faucet supplied water to the turbine wheel to effect rotation thereof and effect corresponding rotation of the magnetically coupled rotatable part of the electrical generator, the nozzle connected to the ozone generator to selectively supply ozone to the water flow therethrough,
        an interface for receiving a one of two sub-components to create, respectfully, the first configuration or the second configuration,
    a first sub-component for attachment to the interface of the primary housing and having a water input port for attachment to a faucet for accepting a flow of pressurized faucet-supplied water and having a water discharge port for selectively discharging ozonated faucet-supplied water or discharging faucet supplied water without ozone mixed therein, a user-operable switch in-circuit with the electrical generator and the ozone generator to supply ozone when in a first state to discharge ozonated faucet-supplied water from the water discharge port or to interrupt electricity to the ozone generator to discharge faucet-supplied water without ozone mixed therein, and
    a second sub-component for attachment to the interface of the primary housing and having a water input port for attachment to a faucet for accepting a flow of pressurized faucet-supplied water and having a first water discharge port for selectively discharging faucet-supplied water and having a second water discharge port for discharging faucet supplied water with ozone mixed therein, the second sub-component further having a user-operable lever movable to a first position to discharge faucet-supplied water from the first water discharge port and movable to a second position to discharge faucet supplied water with ozone mixed therein from the second water discharge port.

5. An apparatus for direct connection to a pressurized-water supply faucet for producing a supply of ozonated water to a discharge port, comprising:

an electrical power generator driven by a rotatable turbine wheel for generating electrical power in response to rotation of the turbine wheel, the turbine wheel mounted for rotation within a fluid-tight turbine chamber having a wall surface on one lateral side of the turbine wheel, the turbine wheel having a plurality of magnets attached thereto facing the wall surface, the electrical power generator having a rotatable part adjacent the wall surface having a plurality of magnets attached thereto facing the wall surface on the side opposite the turbine wheel, the magnets of the turbine wheel and the magnets of the rotatable part magnetically coupled so that rotation of the turbine wheel causes rotation of the rotatable part of the electrical power generator to generate electrical power;

a nozzle for directing a stream of pressurized supply water to the turbine wheel to effect rotation thereof and connected to the ozone generator to introduce ozone into the stream of pressurized supply water; and an ozone generator connected to the electrical power generator to receive electrical power therefrom and generate ozone, the ozone generator connected to the nozzle to introduce ozone into the water stream, the ozone generator having a drying agent in a case having a hole or opening for admitting ambient air therethrough to dry the so-admitted ambient air by the drying agent, a glass tube having a stainless steel coil within the glass tube and positioned concentrically therein by an insulative resin molded supporting structure to provide a uniform clearance between the inner diameter of the glass pipe and the stainless steel coil, and a further glass tube having a smaller-diameter inner glass tube therein and having a space therebetween to define outer and inner glass tubes, the outer glass tube having a thermal material for preventing dew formation.

6. The apparatus of claim 5, wherein the glass tube comprises a quartz glass.

* * * * *